United States Patent [19]

Lyons et al.

[11] 4,375,361

[45] Mar. 1, 1983

[54] PROCESS FOR MAKING A HIGH OCTANE FUEL COMPONENT

[75] Inventors: James E. Lyons, Wallingford; George Suld, Springfield; Robert W. Shinn, Aston; Kenneth A. Scott, Swarthmore, all of Pa.

[73] Assignee: Suntech, Inc., Philadelphia, Pa.

[21] Appl. No.: 133,172

[22] Filed: Mar. 24, 1980

[51] Int. Cl.$^3$ .............................................. C10L 1/18
[52] U.S. Cl. .......................................... 44/70; 560/1; 560/241.1; 44/56; 44/77
[58] Field of Search ............... 44/70, 56, 77; 560/265, 560/241.1, 198, 1; 260/410.9 R, 451

[56] References Cited

U.S. PATENT DOCUMENTS

| | | | |
|---|---|---|---|
| 2,110,078 | 3/1938 | Burwell | 44/57 |
| 2,132,968 | 10/1938 | Penniman | 44/53 |
| 2,970,164 | 1/1961 | Jezl | 260/451 |

*Primary Examiner*—Jacqueline V. Howard
*Attorney, Agent, or Firm*—J. Edward Hess; Donald R. Johnson; Paul Lipsitz

[57] ABSTRACT

A process for converting Udex raffinate to a high octane fuel component by mild, liquid phase oxidation to a product of moderate to low acidity, distilling off a neutral oxidate, esterifying the acidic residue to a neutral product and combining the neutral oxidate and the esterified portion.

26 Claims, 1 Drawing Figure

PROCESS FOR MAKING A HIGH OCTANE FUEL COMPONENT

The selective extraction of aromatics from naphthas is practiced widely. The Udex process utilizing a glycol type solvent has wide commercial use for extracting aromatics of the $C_6$–$C_8$ range. This process is described in Hydrocarbon Processing, September, 1970, p. 248. In conventional practice of this process the hydrocarbon feed stream containing all of the $C_6$–$C_8$ aromatics is introduced at an intermediate level into a countercurrent extraction column in which the solvent phase flows downwardly. The raffinate and extract phases are removed from the top and bottom of the column, respectively. The extract phases are sent to an extractive distillation stripper column from which saturated hydrocarbons together with some aromatic material is stripped overhead. This overhead material is returned to a lower part of the extraction column as reflux. A mixture of high aromaticity containing the $C_6$–$C_8$ aromatics is removed at an intermediate level from the stripper column, while the solvent is recovered from the bottom and recycled to the top of the extraction column. Table I shows some properties and composition of a typical Udex raffinate which comprises primarily a mixture of the various isomers of straight and branched chain hydrocarbons containing five to nine carbon atoms together with a small amount of aromatic, alicyclic and olefinic compounds; e.g. a substantially aromatics-free $C_5$–$C_9$ hydrocarbon.

The raffinate phase of the Udex process has been used heretofore as an additive to a gasoline pool, but because of its low octane value (RON=56, MON=57) it is necessary to add sufficient lead to increase the octane to obtain necessary octane performance. The use of lead as an antiknock additive is being phased out because of environmental considerations and, accordingly, new means for octane improvement is necessary.

It is also known that hydrocarbons may be oxidized to oxygen containing compounds which have value as antiknock agents. For example, U.S. Pat. No. 2,128,910 discloses the addition to gasoline of heavy end products of various oxygenated hydrocarbons such as butane, light petroleum distillates, gas oil and the like which act as a solubilizing agent for alcohols added to gasoline for anti-knock purposes. U.S. Pat. No. 2,132,968 discloses that oxygenated hydrocarbons such as oxygenated petroleum oil or related materials may be used directly as motor fuels or added to gasoline and used as motor fuels. U.S. Pat. No. 3,829,510 discloses the preparation of a high octane gasoline by blending gasoline with alcohols made by reduction of isobutane oxidation products from which esters have been separated. U.S. Pat. No. 3,903,251 discloses the making of a high octane gasoline by adding a mixture of butyl alcohol and butyl acetate made by esterification of a butane oxidation product. However, it has not been shown heretofore how to upgrade a Udex raffinate for use in hydrocarbon fuel as an octane improver.

It has now been found that Udex raffinate may be modified to make it a valuable high octane fuel component having a blending value octane number (BVON) of at least about 100 and generally over 100. In accord with the invention, a Udex raffinate is subjected to a liquid phase oxidation under mild conditions to give a product of moderate to low acidity which is distilled to remove a neutral oxidate product, the acid residue from the distillation being esterified with a lower alkanol and the esterfied portion being combined with the neutral oxidate to yield a high octane fuel additive.

Figure 1:
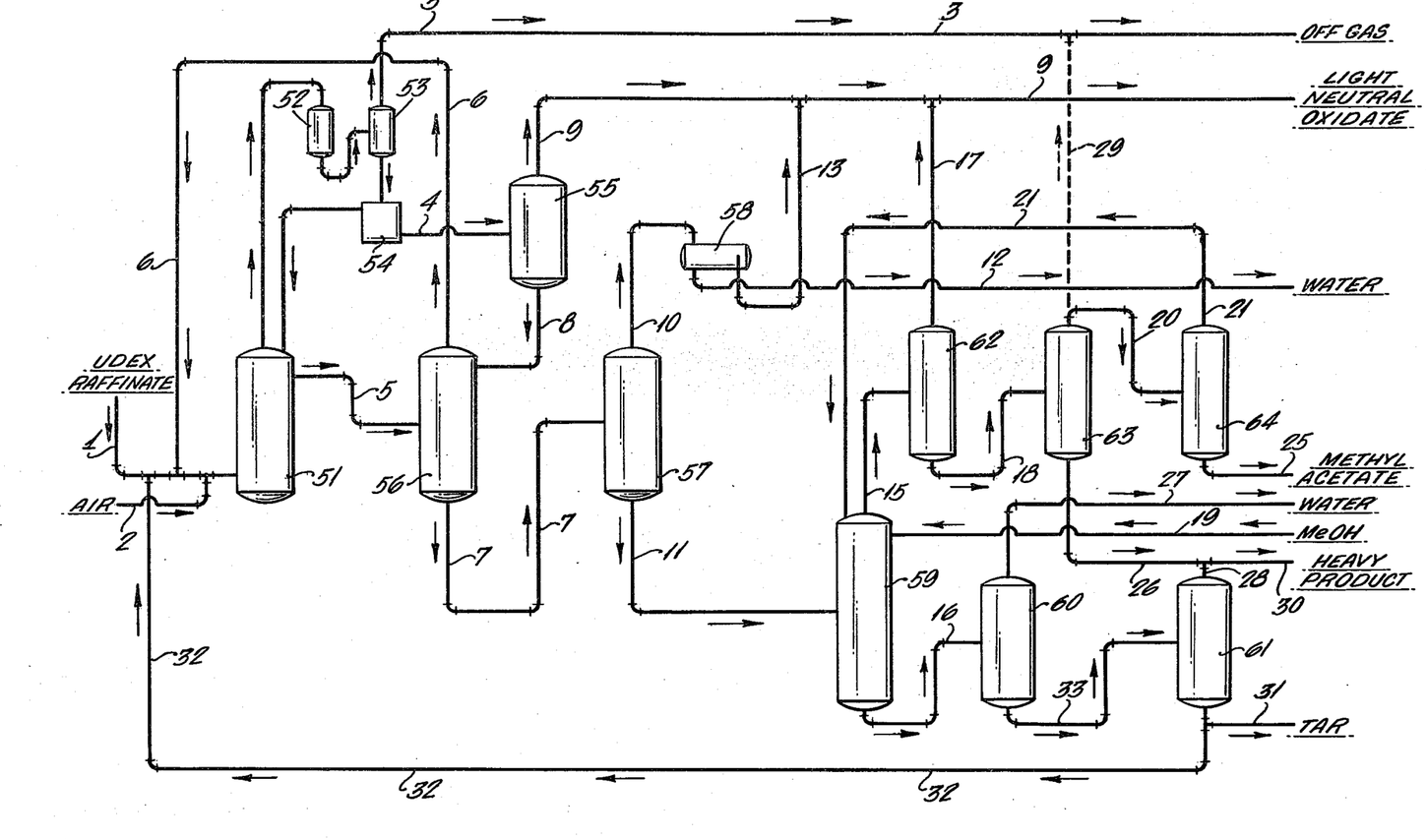

Reference is now made to FIG. 1 to further exemplify the process of the invention. A Udex raffinate (line 1) and air or oxygen (line 2) is taken to an oxidation reactor 51 (batch or continuous, e.g., a series of back-mixed reactors such as continuously stirred reactors or bubble columns) where catalytic liquid phase oxidation occurs under mild conditions of from about 120° to about 160° C. and at about 200 to about 1000 psig, preferably up to about 500 psig pressure. Reaction time will generally be on the order of several hours; e.g., about 2 to about 10 hours and both acidity of the product and conversion is increased with time. In order to achieve conversion of over 50% to oxygenated hydrocarbon and still maintain a relatively low acidity, an oxidation residence time of at least about 4 to 5 hours will be used. The flow rate of air or oxygen through the reactor will generally be from about 3 to about 14 liters per kilogram per minute. While the reaction can be carried out at temperatures above about 145° C. (preferably 160° C.) without a catalyst, the reaction under such conditions may be slow and may require external heat to maintain the process. Thus, it is preferred to operate the process with a catalyst which may be a homogeneous catalyst (i.e. soluble in the reaction medium) or a heterogeneous catalyst. Suitable homogeneous catalysts for the reaction are the typical soluble metal salts used for liquid phase oxidations such as the acetates, benzoates, acetylacetonates or naphthenates of cobalt, nickel, copper, iron, chromium, manganese, vanadium, titanium, molybdenum and the like including mixed metal salts. The heterogeneous catalysts will include similar metals supported on a conventional catalyst support including, preferably, the zeolitic materials which are known in the art. Preferred catalysts are the cobalt and manganese salts and mixed cobalt and copper napthenates and acetylacetonates. When using vanadium catalysts, they are preferably used in batch systems as they tend to cause the formation of greater amounts of water which separates to give two phases. This creates equipment and handling difficulties in a continuous system and thus vanadium catalysts should be avoided in such continuous processes. It will be understood that promoters and initiators may be employed in the oxidation reaction such as, respectively, metal salts and hydroperoxides which are conventionally used. The oxidized product will generally comprise more than sixty percent of neutral product (ketones and alcohols) and less than forty percent of acids. As indicated, this oxidized product will be of low to moderate acidity, being on the order of from about 3 to about 10 milliequivalents of acid per gram depending, at least to some extent, upon the particular catalyst used. In general, manganese acetylacetonate gives a higher acidity than vanadium acetylacetonate and cobalt acetylacetonate is intermediate these two. Generally about 93% to 97% of the hydrocarbons in the Udex raffinate are converted to useful liquid products, the remaining 7% to 3% being burned to CO and $CO_2$ by the oxidation.

Unreacted hydrocarbons and water vapor are taken overhead from the reactor to a condenser 52 and then to a knock-out drum 53 where the CO, $CO_2$, $N_2$ and unreacted oxygen vapors pass overhead (line 3) as off gases. The liquid water and condensed hydrocarbons are taken to a separator 54 where the separated liquid hydrocarbons are returned to the oxidizer. The water, still containing some soluble, low molecular weight oxygen-containing products of the reaction, is taken by line 4 to a fractionating column 55 for stripping off the light, neutral oxidate products (line 9). Fractionating column 55 could, of course, be replaced by a flash distillation unit or other suitable equipment to remove the light neutral oxidate product. The remaining water from this separation step, which is now essentially free of any oxidized product, is passed through line 8 to a phase separator 56 containing the major portion of the oxidation products obtained from the oxidation reactor through line 5. The upper unreacted hydrocarbon layer in the phase separator 56 is returned to the reactor through line 6 and the lower aqueous layer containing the water soluble reaction products (e.g. acids and other liquid products) is taken through line 7 to a neutral product separation column 57. Here, water and light neutral products such as acetone are distilled off and taken through line 10 to a separator 58 and the separated light products taken by line 13 to the light neutral oxidate product output line 9. Water is taken off at line 12, as shown.

The water soluble acids are taken from the bottom of separator 57 through line 11 to a distillation reactor 59 where esterification produces a neutral product by reaction of the acids with a lower alkanol such as methanol added to the reactor through line 19.

The esterification will be carried out under conditions of reactive distillation using sulfuric acid (50°-66° Be) as catalyst. Reference is made to U.S. Pat. No. 1,400,849 (A. A. Backhaus, 1921) and to the article in *Industrial and Engineering Chemistry* 24 No. 10, p. 1099 (1932) for further details. In general, the reactive distillation is carried out at atmospheric pressure and thus methyl formate distills over at about 33° C., an azeotrope of methyl acetate with methanol distills at about 53° C., methyl acetate at about 57° C., and the like.

The higher molecular weight components from the esterification (e.g. $C_4$ esters and higher) are taken from the reactor through line 16 to distillation column 60 where water is distilled off (line 27). The remaining heavy product portion is passed through line 33 to a distillation column 61 from which the heavy products of the process are distilled off (line 28). The residue from the distillation is removed as tar through drag stream line 31, part of which tar material is recycled through line 32 to the oxidizer for further oxidation to useful products. The distillate (line 28) from Column 31 is combined with stream 26 to give the total heavy product in line 30.

The low molecular weight esters formed by the esterification (e.g. methyl formate, methyl acetate, and smaller amounts of heavier esters; e.g. methyl propionate and methyl butyrate) together with some methanol are taken overhead from the esterification reactor 59 through line 15 to distillation column 62 so as to distill off the light products which are taken by line 17 for addition to light product line 9. The bottoms from column 62 comprising methanol and low molecular weight esters (e.g. methyl acetate and methyl propionate) are taken through line 18 to a second distillation column 63 where esters heavier than methyl acetate (e.g. methyl butyrate) are removed as bottoms and taken to heavy products line 26.

The overhead from column 63 comprised of methanol and methyl acetate may be taken directly to the neutral oxidate line 9 as shown by dashed line 29, or, as shown in the figure, may be taken through line 20 to a third distillation column 64 where the methanol distilled off is recycled through line 21 to the esterification reactor. Bottoms product from column 64 is methyl acetate, a valuable industrial chemical. It will be understood, of course, that other appropriate separation steps may be used to recover the methyl acetate. For example, azeotropic distillation techniques, say with hexane, could be used to break out the desired ester product.

In order to prepare an improved fuel composition, the light neutral oxidate from line 9 and heavy oxidate product of the process from line 30 are simply mixed with a hydrocarbon fuel. Alternatively, the heavy residual oxygen-containing products in line 16 may be treated by allowing the material to separate into an aqueous and an oil layer and extracting the oil (e.g. the heavy oxygen-containing components) layer with gasoline, to which extract the light neutral oxidate would be added to give a gasoline containing the oxygen containing compounds. Other variations of how to handle and mix the oxidate and a hydrocarbon fuel will be obvious to the art worker.

The amount of oxidate in the fuel to give improved octane performance will, of course depend upon the desired octane desired for the final fuel product. Since the oxidate has a high blending value octane number the Udex raffinate oxidate gives a significant increase to hydrocarbon fuels, particularly in leaded gasoline.

The properties and major components of a typical Udex raffinate are shown in Table I and the reaction conditions for use with a typical Udex raffinate oxidation in accord with the invention is given in Table II. Table III lists the specific organic products obtained from such typical Udex raffinate oxidation.

TABLE I

PROPERTIES & MAJOR COMPONENTS OF TYPICAL "UDEX" RAFFINATE

| Properties: | Octane Number (clear) RON = 56, MON = 57 Density 0.68 Boiling Range 30-175° C. (85-350° F.) | |
|---|---|---|
| | | Percent |
| Composition: | Normals | 20-30 |
| | Singly-branched | 40-50 |
| | Multiply-branched with tert. hydrogen | 5-15 |
| | Multiply-branched without tert. hydrogen | 3-8 |
| | Alicyclic | 3-8 |
| | Aromatics | 4-9 |
| | Olefins | 1 |
| | $C_9$ | 2-4 |
| | | Percent |
| Typical Normals Breakdown: | Pentane | 0.7 |
| | Hexane | 9.2 |
| | Heptane | 10.2 |
| | Octane | 3.9 |
| | Nonane | 0.2 |
| | | 24.2 |

Typical Breakdown of major branched components:

| | Percent |
|---|---|
| 2-Methylpentane | 7.1 |
| 3-Methylpentane | 5.9 |
| 2,3-Dimethylpentane | 3.7 |
| 2-Methylhexane | 8.8 |
| 3-Methylhexane | 11.4 |
| 2-Methylheptane | 3.3 |
| 3-Methylheptane | 5.6 |
| 4-Methylheptane | 1.9 |

TABLE I-continued

PROPERTIES & MAJOR COMPONENTS OF TYPICAL "UDEX" RAFFINATE 47.7

TABLE II

TYPICAL UDEX RAFFINATE OXIDATION REACTION

| CONDITIONS: | CATALYST - Cobalt acetylacetonate CO(ACAC)$_3$ (2 GRAMS/L) INITIATOR - t-BUTYLHYDROPEROXIDE OXIDANT - AIR PRESSURE - 400 PSI FLOW RATE - 2 L/MIN TEMPERATURE - 145° C. TIME - 5 HRS. | |
|---|---|---|
| CONVERSION OF RAFFINATE TO PRODUCTS: | | 60% |
| PRODUCT COMPOSITION: | | |
| % HYDROCARBON BURNED: | | 7% |
| % HYDROCARBON CONVERTED TO LIQUIDS: | | 93% |
| BREAKDOWN OF LIQUID ORGANIC PRODUCT (WT. %) | | |
| ACIDS | | 31% |
| KETONES, ALCOHOLS & ESTERS | | 61% |
| TAR FORMERS | | 8% |
| PHASE DISTRIBUTION: | | |
| HYDROCARBON (UPPER) PHASE | | 40% |
| AQUEOUS (LOWER) PHASE | | 60% |

TABLE III

ORGANIC PRODUCTS FROM TYPICAL UDEX RAFFINATE BATCH OXIDATION (COMBUSTION PRODUCTS NOT INCLUDED)

| PRODUCT | SELECTIVITY |
|---|---|
| ACETONE | 11.7 |
| LIGHT ESTERS | 4.6 |
| MEK | 9.5 |
| ETHANOL | 1.9 |
| 2-PENTANONE | 5.2 |
| C$_5$-C$_8$ ALCOHOLS AND KETONES | 27.1 |
| ACETIC ACID | 20.2 |
| PROPIONIC ACID | 3.7 |
| BUTYRIC ACID | 3.0 |
| HEAVY ACIDS, TARS AND OTHERS | 13.1 |
| | 100.0 |

In order to illustrate the invention in more detail the following examples are given.

EXAMPLE 1

Oxidation of Udex Raffinate

Udex raffinate was charged to a reactor and oxidized with a mixture of 21% oxygen and 79% nitrogen at a flow rate of 2 liter per minute and initiated with t-butylhydroperoxide by adding to the Udex raffinate 20 ml. of a solution containing 10% by volume of the initiator and 90% Udex raffinate. Table IV which follows indicates the various catalysts used, other reaction conditions and the results obtained.

EXAMPLE 2

A typical flow sheet for the process corresponding to the flow diagram of the drawing is shown in Table V. The column numbers of Table V refer to the flow lines of the drawing which shows the barrels per day of the major components of the process in each of the various sections of the overall process.

EXAMPLE 3

Octane Improvement With Oxidized Udex Raffinate

An unleaded base stock gasoline having a road octane number (RON) of 92.8, a motor octane number (MON) of 83.8 and R+M/2 (i.e. RON+MON/2) of 88.3 was blended with the blending component obtained by the oxidation of Udex raffinate in accord with the process of the invention. Table VI gives the data obtained which indicates the high blending value octane number (BVON) for the raffinate oxidate.

TABLE IV

OXIDATIONS OF UDEX RAFFINATE

| Catalyst | Cat. Conc. (g/l) | Press. (PSI) | Temp. (C.) | Grams Charged | Products (GMS) UL | LL | Total | Conv. of UL (Wt. %) | Acidity UL | LL | Oxygen in UL (Wt. %) |
|---|---|---|---|---|---|---|---|---|---|---|---|
| CoSt, Co(AcAc), Mn(AcAc) | 1,1,2 | 400 | 158 | 342 | 222 | 144 | 366 | 51 | 1.13 | 5.13 | 7.1 |
| CoSt, Co(AcAc), Mn(AcAc) | 1,1,2 | 600 | 145 | 331 | 198 | 209 | 402 | 50 | 0.95 | 6.79 | 8.4 |
| Fe(AcAc)₂, Fe(AcAc)₃, Co(AcAc)₃ | 1,1,2 | 400 | 145 | 338 | 197 | 205 | 402 | 50 | 0.87 | 5.08 | 8.2 |
| Cu(OAc), Cr(OAc)₂ | 1,1 | 400 | 145 | 338 | 205 | 140 | 345 | 49 | 0.87 | 5.08 | 8.2 |
| Cu(AcAc), Cu(OAc)₂, Cr(AcAc)₃ | 1,1,2 | 400 | 145 | 341 | 123 | 224 | 341 | 67 | 0.93 | 5.47 | 8.2 |
| Cr(AcAc)₃ | 2 | 400 | 145 | 388 | 177 | 221 | 398 | 55 | 0.98 | 4.92 | 8.7 |
| Mo(AcAc)₃ | 1.5 | | | | 200 | 10 | | | 0.21 | | 2.5 |
| Mn(AcAc)₃ | 8 | 400 | 145 | 338 | 202 | 199 | 401 | 49 | 1.09 | 8.24 | 7.4 |
| VO(AcAc)₂ | 2 | 400 | 145 | 340 | 192 | 198 | 390 | 52 | 0.57 | 4.63 | 7.6 |
| KM_nO₄ | 8 | 400 | 145 | 388 | 252 | 120 | 372 | 39 | 1.20 | 8.36 | 6.5 |
| Cr(AcAc)₃ | 2 | 400 | 135 | 340 | 200 | 202 | 402 | 50 | .98 | 5.90 | 7.5 |
| Cr(AcAc)₃ | 2 | 400 | 125 | 339 | 297 | 55 | 352 | 29 | .73 | 4.40 | 6.8 |
| VO(AcAc)₂ | 2 | 400 | 135 | 341 | 282 | 161 | 393 | 43 | .46 | 5.44 | 6.1 |
| None | — | 400 | 145 | 338 | 178 | 236 | 414 | 54 | | | 9.3 |
| Cr(AcAc)₃ | 2 | 400 | 155 | 340 | 168 | 240 | 408 | 57 | 1.45 | 5.26 | 10.4 |
| V-Co Zeol(f) | 20 | 400 | 145 | 126 | 199 | | 325 | | 1.05 | 4.49 | 7.5 |
| Co(AcAc)₃ | 2 | 400 | 145 | 341 | 166 | 245 | 411 | 57 | 1.00 | 4.88 | 8.0 |
| None | — | 400 | 165 | 337 | 175 | 224 | 399 | 55 | 1.25 | 4.88 | 9.6 |
| Mn(AcAc)₃ | 2 | 400 | 145 | 339 | 179 | 223 | 402 | 54 | 0.87 | 4.87 | 8.0 |
| Fe(AcAc)₃ | 2 | 400 | 145 | 540 | 157 | 253 | 410 | 59 | 1.03 | 7.34 | 8.0 |
| TiO(AcAc)₃ | 2 | 400 | 145 | 338 | 235 | 146 | 381 | 44 | 0.89 | 5.51 | 7.4 |
| Ni(AcAc)₂ | 2 | 400 | 145 | 340 | 250 | 126 | 376 | 39 | 0.86 | 5.40 | 7.2 |
| Co(AcAc)₃ | 2 | 400 | 125 | 340 | 245 | 143 | 388 | 40 | 0.82 | 4.97 | 7.1 |
| Co-V Zeol(g) | 20 | 400 | 125 | 336 | 227 | 119 | 346 | 44 | 0.99 | 5.19 | 7.6 |
| Co(AcAc)₃(i) | 2 | 600 | 145 | 338 | 293 | 78 | 381 | 30 | 0.79 | 5.45 | 8.1 |
| Co(AcAc)₃(i) | 2 | 400 | 145 | 335 | 292 | 56 | 348 | 29 | 0.71 | 3.80 | 8.3 |
| Cr(AcAc)₃(i) | 2 | 400 | 145 | 340 | 277 | 73 | 350 | 34 | 0.17 | 3.55 | 8.5 |
| Mn(AcAc)₃(i) | 2 | 400 | 145 | 342 | 288 | 78 | 366 | 33 | 0.74 | 4.00 | 7.7 |
| Co(AcAc)₃(h) | 2 | 400 | 145 | 340 | 177 | 219 | 396 | 55 | 1.03 | 4.15 | 9.2 |
| Co(AcAc)₃(i) | 2 | 400 | 125 | 340 | 235 | 86 | 321 | 43 | 0.71 | 4.24 | 7.2 |

| Catalyst | GC Anal L.L. (Area %) Acetone | MEK | Water | Acetic Acid | Propionic Acid | Butyric Acid(c) | GC Anal U.L. (Area %) Acetone | MEK | 2-Pentanone | Lt K & A(d) | HUY K & A(e) |
|---|---|---|---|---|---|---|---|---|---|---|---|
| CoSt, Co(AcAc), Mn(AcAc) | 8.3 | 2.3 | 23.9 | 20.6 | 11.3 | 3.4 | | | | | |
| CoSt, Co(AcAc), Mn(AcAc) | 9.5 | 4.5 | 20.3 | 21.2 | 6.9 | 2.8 | | | | | |
| Fe(AcAc)₂, Fe(AcAc)₃, Co(AcAc)₃ | 9.1 | 4.6 | 18.7 | 18.0 | 7.5 | 3.1 | | | | | |
| Cu(OAc), Cr(OAc)₂ | 10.7 | 5.2 | 19.5 | 21.8 | 8.0 | 3.0 | | | | | |
| Cu(AcAc), Cu(OAc)₂, Cr(AcAc)₃ | 8.8 | 5.1 | 16.3 | 21.3 | 8.1 | 4.2 | | | | | |
| Cr(AcAc)₃ | | | | | | | | | | | |
| Mo(AcAc)₃ | | | | | | | | | | | |
| Mn(AcAc)₃ | 5.8 | 1.2 | 21.2 | 30.1 | 14.9 | 3.6 | | | | | |
| VO(AcAc)₂ | 11.3 | 4.7 | 30.6 | 19.0 | 5.6 | 2.0 | | | | | |
| KM_nO₄ | 3.3 | 1.2 | 30.5 | 29.6 | 14.1 | 2.5 | | | | | |
| Cr(AcAc)₃ | 8.0 | 4.7 | 21.6 | 28.8 | 10.6 | 3.4 | | | | | |
| Cr(AcAc)₃ | 6.2 | 3.7 | 36.3 | 15.9 | 5.5 | 2.0 | | | | | |
| VO(AcAc)₂ | 11.3 | 4.1 | 30.3 | 20.0 | 8.4 | 2.1 | | | | | |
| None | 10.8 | 5.2 | 23.6 | 27.0 | 8.0 | 3.1 | | | | | |
| Cr(AcAc)₃ | 10.3 | 5.5 | 24.5 | 23.7 | 8.1 | 2.5 | | | | | |
| V-Co Zeol(f) | 9.3 | 5.2 | 27.1 | 19.8 | 6.3 | 2.2 | | | | | |

TABLE IV-continued

| | | | | | | | | | |
|---|---|---|---|---|---|---|---|---|---|
| Co(AcAc)₃ | 10.4 | 5.2 | 26.3 | 21.1 | 6.5 | 2.1 | | | |
| None | 12.0 | 7.6 | 24.5 | 11.0 | 6.7 | 1.9 | | | |
| Mn(AcAc)₃ | 8.9 | 2.3 | 21.7 | 29.9 | 11.4 | 3.0 | | | |
| Fe(AcAc)₃ | 10.5 | 5.1 | 24.6 | 23.1 | 8.8 | 3.1 | | | |
| TiO(AcAc)₃ | 9.3 | 5.2 | 26.2 | 22.7 | 8.0 | 2.3 | | | |
| Ni(AcAc)₂ | 9.7 | 5.5 | 22.1 | 22.2 | 8.0 | 2.9 | | | |
| Co(AcAc)₃ | 9.3 | 5.0 | 23.3 | 21.4 | 8.0 | 2.6 | | | |
| Co-V Zeol(g) | 7.8 | 4.7 | 26.3 | 24.6 | 8.1 | 2.9 | | | |
| Co(AcAc)₃(f) | 8.4 | 4.6 | 36.9 | 16.7 | 3.9 | 1.9 | | | |
| Co(AcAc)₃(f) | 7.2 | 4.3 | 37.4 | 16.2 | 3.4 | 2.8 | 2.7 | 2.8 | 1.3 |
| Cr(AcAc)₃(f) | 8.5 | 4.8 | 32.6 | 17.9 | 4.1 | 2.4 | 2.9 | 2.4 | 1.5 |
| Mn(AcAc)₃(f) | 8.1 | 4.8 | 31.7 | 18.3 | 5.0 | 2.3 | 2.6 | 2.1 | 1.4 |
| Co(AcAc)₃(h) | 10.3 | 6.5 | 27.2 | 19.7 | 6.3 | 1.6 | 3.4 | 2.7 | 1.6 |
| Co(AcAc)₃(i) | 8.0 | 5.1 | 33.0 | 14.1 | 4.8 | 2.3 | 2.3 | 2.1 | 1.5 |

Also: 2.4 (Cr(AcAc)₃(f) row, far right), 13.8 (Co(AcAc)₃(i) row, far right)

Legend:
UR = Udex Raffinate
UL = Upper Layer (Hydrocarbon Layer)
LL = Lower Layer (Aqueous Acid Layer)
GC Anal = Gas Chromotograph Analysis
CHG = Charge
CoSt = Cobalt Stearate
AcAc = Acetylacetonate
OAc = Acetate
(a)% Conv. UR = [Wt CHG − (.8 × Wt UL + .05 × Wt LL)] ÷ Wt CHG × 100
(b)ACIDITY = meq NaOH/gm required to neutralize
(c)Slight amount of unknown impurity present
(d)Ketones and alcohols of 5 carbon atoms and less
(e)Ketones and alcohols of 6 carbon atoms and more
(f)A sodium zeolite exchanged 16 times with vanadium and once with cobalt
(g)A sodium zeolite exchanged 16 times with cobalt and once with vanadium
(h)No initiator used
(i)Gas Composition 10% oxygen and 90% nitrogen

TABLE V

FLOW DIAGRAM (Barrels per Day) FOR UDEX RAFFINATE OXIDATION

| | 1 | 2 | 3 | 4 | 5 | 6 | 7 | 8 | 9 | 10 | 11 | 12 | 13 | 15 | 16 | 17 |
|---|---|---|---|---|---|---|---|---|---|---|---|---|---|---|---|---|
| Udex raffinate | 53,564 | | | 3,506 | 5,000 | 4,000 | 1,000 | | 3,506 | 1,000 | | 50 | 950 | | | |
| Acetone | 1,000 | | | 5,100 | 8,378 | 1,000 | 7,401 | | 5,100 | 7,401 | | 101 | 7,300 | | | |
| Methyl-ethyl-ketone | 500 | | | 1,400 | 4,919 | 500 | 4,419 | | 1,400 | 4,419 | | 69 | 4,350 | | | |
| Ethyl acetate | 1,041 | | | | 1,041 | 2,082 | 1,041 | 1,041 | | 1,041 | 1,041 | 41 | 1,000 | | | |
| Methyl acetate | 1,400 | | | 1,868 | 4,200 | 1,400 | 2,800 | | 1,868 | 2,800 | | 100 | 2,700 | 44,350 | | |
| Oxy-isomers (a) | 5,782 | | | | 11,564 | 5,782 | 5,782 | | | | 5,782 | | | | 7,228 | |
| Formic acid | 500 | | | | 3,402 | 500 | 2,902 | | | | 2,902 | | | | | |
| Acetic acid | 2,400 | | | | 26,055 | 2,400 | 23,655 | | | | 23,655 | | | | | |
| Propionic acid | 1,200 | | | | 5,868 | 1,200 | 6,688 | | | | 4,688 | | | | | |
| Butyric acid | 1,041 | | | | 2,082 | 1,041 | 1,041 | | | | 1,041 | | | | 1,041 | |
| Heavy acids (b) | 1,340 | | | | 4,021 | 1,340 | 2,681 | | | | 2,681 | | | | 1,500 | |
| Tar | 4,731 | | | | 6,308 | | 6,308 | | | | 6,308 | | | | 6,308 | |
| Water | 850 | | | 12,370 | 850 | 850 | 12,370 | 12,370 | | | | 12,220 | 150 | | 9,936 | |
| $O_2$ | | 48,026 | 4,803 | | | | | | | | | | | | | |
| $N_2$ | | 180,670 | 180,670 | | | | | | | | | | | | | |
| $CO + CO_2$ | | 7,668 | | | | | | | | | | | | | | |
| Methanol | | | | | | | | | | | | | | | 11,088 | |
| Methyl-propionate | | | | | | | | | | | | | | | 5,553 | |
| Methyl butyrate | | | | | | | | | | | | | | | 1,204 | |
| Heavy acid esters (c) | | | | | | | | | | | | | | | 2,955 | |
| Methyl formate | | | | | | | | | | | | | | | 3,786 | 3,786 |

| | 18 | 19 | 20 | 21 | 22 | 23 | 24 | 25 | 26 | 27 | 28 | 30 | 31 | 32 | 33 |
|---|---|---|---|---|---|---|---|---|---|---|---|---|---|---|---|
| Udex raffinate | | | | | 4,456 | | | | | | | | | | |
| Acetone | | | | | 12,400 | | | | | | | | | | |
| Methyl-ethyl-ketone | | | | | 5,750 | | | | | | | | | | |
| Ethyl acetate | | | | | 2,041 | | | | | | | | | | |
| Methyl acetate | | | 44,350 | 16,631 | 4,568 | | | 23,719 | | | | 1,459 | | | |
| Oxy-isomers (a) | | | | | | | | | | | 7,228 | 5,782 | | | 7,228 |
| Formic acid | | | | | | | | | | | | | | | |
| Acetic acid | | | | | | | | | | | | | | | |
| Propionic acid | | | | | | | | | | | | | 67 | 133 | 200 |
| Butyric acid | | | | | | | | | | | | | 100 | 200 | 300 |
| Heavy acids (b) | | | | | | | | | | | | | 1,577 | 4,731 | 6,308 |
| Tar | | | | | 150 | | | | | | | 9,936 | | | |
| Water | | | | | | | | | | | | | | | |
| $O_2$ | | | | | | | | | | | | | | | |
| $N_2$ | | | | | | | | | | | | | | | |
| $CO + CO_2$ | | | | | | | | | | | | | | | |
| Methanol | 11,088 | 17,664 | 11,088 | 11,088 | | | | | | | | | | | |
| Methyl-propionate | 5,553 | | | | | | | | | 5,553 | | 5,553 | | | |
| Methyl butyrate | | | | | | | | | | | 1,204 | 1,204 | | | 1,204 |
| Heavy acid esters (c) | | | | | | | | | | | 2,955 | 2,955 | | | 2,955 |

TABLE V-continued

Methyl
Formate (a) = isomeric $C_5$-$C_8$ alcohols and ketones
(b) = aromatic carboxylic acids, aromatic and aliphatic dicarboxylic acids and other heavy acid products
(c) = methyl esters of the acids described in (b)

TABLE VI
OCTANE IMPROVEMENT WITH UDEX RAFFINATE OXIDATES

| ADDITIVE CONCENTRATION % | ΔRON | Δ(R + M)/2 | ΔMON | | BVON (R + M)/2 |
|---|---|---|---|---|---|
| A | | | | | |
| 1 | 0.28 | 0.19 | 0.19 | | 107 |
| 3 | 0.55 | 0.39 | 0.23 | | 101 |
| 5 | 1.05 | 0.82 | 0.58 | | 105 |
| 7 | 1.43 | 1.18 | 0.93 | | 105 |
| 10 | 1.83 | 1.52 | 1.20 | | 103 |
| 15 | 2.43 | 2.22 | 2.00 | Ave. | 104 |
| B | | | | | |
| 3 | 0.43 | 0.52 | 0.60 | | 105 |
| 5 | 0.70 | 0.72 | 0.73 | | 103 |
| 7 | 0.95 | 0.98 | 1.0 | | 102 |
| 10 | 1.35 | 1.35 | 1.35 | | 102 |
| 15 | 1.75 | 1.70 | 1.65 | | 99.5 |
| | | | | Ave. | 102 |

A Blending component of Udex raffinate oxidation containing approximately 12% by weight methanol from the esterification. All numbers in this section are averages of four determinations.
B Blending component of Udex raffinate oxidation with no excess alcohol. The numbers for 3,5, and 10% levels are averages of four determinations, and 7 and 15% levels of two determinations.

EXAMPLE 4

Continuous Oxidation System

Into a one liter stirred autoclave there was placed 550 ml of Udex Raffinate containing, in solution 500 ppm of manganese in the form of a soluble manganese naphthenate.

The reactor was heated under nitrogen to 160° C. and then the nitrogen was displaced by air flowing at about 4 l/min.

Then, about 2 ml of t-butyl hydroperoxide dissolved in some Udex Raffinate was pumped into the reactor as the initiator for the oxidation reaction and in a few minutes the oxidation reaction began as indicated by an exotherm.

The oxidation reaction was run continuously for 105 hours with continuous product take-off. Recirculation of the unreacted hydrocarbon layer from a product separator to the oxidation reactor was made continuously. At the same time a quantity of fresh Udex Raffinate containing 500 ppm dissolved manganese naphthenate and equal in volume to the oxidized product removed from the separator was continuously charged into the reactor.

The oxidized product composition comprised, on average, approximately 10% acetone, 4% methylethyl ketone, 30% acetic acid, 14% $C_3$ to $C_4$ acids and 12% water, the balance being other unidentified oxidation products.

After separation of the acid materials, they were esterified with methanol by reactive distillation in a 15-tray Oldershaw 2" column at a reflux ratio of about 5:1.

Table VII gives data on the oxidation based on the total volume of Udex Raffinate charged and Table VIII gives further data on the product work up.

TABLE VII
Udex Raffinate Oxidation - Continuous Run Using
Mn—Naphthenate Catalyst And t-Butyl Hydroperoxide Initiator

| | |
|---|---|
| Total Udex Raffinate Charged | 16,050 ml.(11,395 g.) |
| Oxidized Product | 15,350 ml.(15,311 g.) |
| Product Rate (ml/hr.) | 70–209 (Avg.140) |
| Temperature | 160–170° C. |
| Pressure | 400 Psi |
| Off Gas Rate (l/min) | 3.5–4.5 |
| CO, $CO_2$ Make (%) | 1.0–4.0 |
| Average Acidity (meq./g) | 8.0 |

TABLE VIII
Product Summary of Example 4

| | |
|---|---|
| Charge of Acid Product | 7725 ml(7985 g) |
| Products Obtained: | |
| Light Solvent plus Light Ester | 7770 ml(6848 g) |
| Heavy Ester plus Heavy Oil | 447 ml(406 g) |
| Residue | 64 g. |

EXAMPLE 5

Following the essential details of Example 4 oxidation of Udex Raffinate was carried out continuously using a cobalt naphthenate catalyst. Table IX gives the data. Product work-up comprised the usual steps of stripping light solvent, esterifying and distilling light ester and vacuum stripping to obtain the heavy oxidate cut. The three fractions were then blended to give the finished high octane fuel component. For each kilogram of raffinate oxidized, 1.44 kilograms of aqueous oxidate was obtained which yielded 1.1 kilograms of finished high octane fuel component on work-up. Table X gives data on this downstream processing.

TABLE IX
CONTINUOUS COBALT NAPHTHENATE CATALYZED OXIDATION OF UDEX RAFFINATE

| Conditions | |
|---|---|
| T = 150° C. | |
| P = 400 Psig | |
| Air Flow = 3.5 l/Min | |
| Catalyst = Cobalt Naphthenate-50 ppm | |
| Time on Stream | |
| 124 Hours | |

| Charge | Weight(Gms) |
|---|---|
| Udex Raffinate | 12495 |
| Unreacted Charge Carried Out In Off-Gas | 722 |
| Effective Charge | 11773 |
| Gaseous Products | |
| Grams Raffinate Burned to $CO/CO_2$ | 453 |
| Raffinate Oxidized to Liquid Product | 11320 |
| Liquid Products | |
| Aqueous Oxidate | 16965 |
| Water Layer Removed by Distillation During Run | 700 |
| Total Liquid Product | 17,665 |
| Production Rate: 145 ml/hr | |
| Liquid Product Acidity: ~30% (5.0 meq/8) | |
| Burn: 6% of Raffinate Charged | |

TABLE X
DOWNSTREAM PROCESSING OF THE OXIDATE FROM CONTINUOUS COBALT NAPHTHENATE CATACYZED OXIDATION OF UDEX RAFFINATE

| | Weight(Gms) |
|---|---|
| CHARGE | |
| Aqueous oxidate charged | 15741 |
| Methanol charged | 3950 |
| Inorganics (Na$_2$SO$_4$ + Excess NaCO$_3$) | 150 |
| | 19841 |
| PRODUCT | |
| Light solvent, L.S. | 4561 |
| Light ester, L.E.[a] | 4179 |
| Methanol co-distilled with L.E. | 1791 |
| Water of esterification[b] | 1417 |
| All other water layers[c] | 3028 |
| Heavy oxidate, H.O. | 3238 |
| Residue (Tar) | 810 |
| Distillation traps | 100 |
| Aliquots for analysis | 50 |
| | 19174 |
| MATERIAL BALANCE | |
| [(Total wt. in. ÷ Total wt. out) × 100] < 96.6% | |
| HIGH OCTANE FUEL COMPONENT YIELD | |
| (L.S. + L.E. + H.O.) = 11978 gms. | |

[a]From GC scans on a methanol-free basis.
[b]Calc. from esterification of 15741 gm. oxidate containing 5.0 meq. acid/gm.
[c]Total water layers (containing approximately 10% organics minus water of esterification).

Typical vapor pressure, corrosivity and other properties for the fuel containing the Udex raffinate oxidate and is shown in Table XI which data were obtained with the fuel composition B of Table VI.

TABLE XI

| | | |
|---|---|---|
| BVON: | 3–10% | 102 |
| RVP: | 5% | 10.9 |
| BVRVP*: | | 20 (EST.) |
| CORROSIVITY: | 5% | R$_1$ DYNAMIC, R$_4$ STATIC |
| HAZE T. °F.: | 5% | 38 |

*BVRVP = Blending Value Reid Vapor Pressure

The invention claimed is:

1. A process for converting a mixture of substantially aromatics-free branched and straight chain C$_5$-C$_9$ hydrocarbons to a high octain fuel component having a blending value octane number of at least about 100 by mild, liquid phase oxidation at a temperature between about 120° and about 160° C. at about 200 to about 1000 psig pressure to a product of moderate to low acidity, distilling off a neutral oxidate, esterifying the residue of said distillation with a lower alkanol to a neutral product and combining the neutral oxidate and the esterified product.

2. A process for converting Udex raffinate to a high octane fuel component having a blending value octane number of at least about 100 by mild, liquid phase oxidation with a metal oxidation catalyst at a temperature between about 120° and about 160° C. and at about 200 to about 500 psig pressure to a product of moderate to low acidity, distilling off a neutral oxidate, esterifying the residue from said distillation with methanol to a neutral product and combining the neutral oxidate and the esterified product.

3. The process of claim 2 wherein the catalyst is a metal acetylacetonate.

4. The process of claim 2 wherein the catalyst is manganese acetylacetonate.

5. The process of claim 2 wherein the catalyst is cobalt acetylacetonate.

6. The process of claim 2 wherein the catalyst is vanadylacetylacetonate.

7. The process of claim 2 wherein the catalyst is a metal naphthenate.

8. The process of claim 2 wherein the catalyst is a cobalt naphthenate.

9. The process of claim 2 wherein the catalyst is a manganese naphthenate.

10. The process of claim 2 wherein the catalyst is a vanadium naphthenate.

11. A fuel component having a blending value octane number of at least about 100 obtained by the liquid phase oxidation of Udex raffinate at a temperature between about 120° and about 160° C. at about 200 to about 1000 psig pressure to a product of low acidity, distilling off a neutral oxidate, esterifying the residue of said distillation with methanol to a neutral product and combining the neutral oxidate and the esterified product.

12. The fuel component of claim 11 wherein the Udex raffinate is oxidized in the presence of a metal oxidation catalyst at a temperature between about 120° and about 160° C. and at about 200 to about 500 psig pressure.

13. The fuel component of claim 12 wherein the catalyst is a metal acetylacetonate.

14. The fuel component of claim 12 wherein the catalyst is manganese acetylacetonate.

15. The fuel component of claim 12 wherein the catalyst is cobalt acetylacetonate.

16. The fuel component of claim 12 wherein the catalyst is vanadium acetylacetonate.

17. The fuel component of claim 12 wherein the catalyst is a metal naphthenate.

18. The fuel component of claim 12 wherein the catalyst is cobalt naphthenate.

19. The fuel component of claim 12 wherein the catalyst is manganese naphthenate.

20. The fuel component of claim 12 wherein the catalyst is vanadium naphthenate.

21. A motor fuel comprising gasoline and an octane increasing amount of an octane increasing component having a blending value octane number of at least about 100 obtained by the liquid phase oxidation of a mixture of substantially aromatics-free branched and straight-chain C$_5$-C$_9$ hydrocarbons at a temperature between about 120° and about 160° C. at about 200 to about 1000 psig pressure to a product of low acidity, distilling off a neutral oxidate, esterifying the residue of said distillation with a lower alkanol to a neutral product and combining the neutral oxidate and the esterified product.

22. A motor fuel comprising gasoline and an octane increasing amount of an octane increasing component having a blending value octane number of at least about 100 obtained by the liquid phase oxidation of Udex raffinate at a temperature between about 120° and about 160° C. at about 200 to about 1000 psig pressure to a product of low acidity, distilling off a neutral oxidate, esterifying the residue of said distillation with methanol to a neutral product and combining the neutral oxidate and the esterified product.

23. The motor fuel of claim 22 wherein the oxidation is carried out with a metal oxidation catalyst at a temperature between about 120° and 160° C. and at about 500 psig pressure.

24. The motor fuel of claim 23 wherein the catalyst is selected from the group of metal acetylacetonates and metal naphthenates.

25. The motor fuel of claim 24 wherein the metal of said catalyst is selected from the group of cobalt, manganese and vanadium.

26. A process for converting Udex raffinate to a high octane fuel component having a blending value octane number of at least about 100 and volatility in the range of gasoline by mild, liquid phase oxidation with a metal oxidation catalyst at a temperature between about 120° and about 160° C. and at about 200 to about 500 psig pressure to a product of moderate to low acidity, thereafter (a) distilling off a neutral oxidate (b) esterifying the residue from said distillation by a reactive distillation to give low molecular weight methyl esters which are distilled off as a light product, (c) distilling the residue from said reactive distillation to obtain a heavy oxidate product, combining the products obtained by said steps a, b, and c to obtain said high octane fuel component.

* * * * *